(12) United States Patent
Hill

(10) Patent No.: US 6,394,984 B1
(45) Date of Patent: May 28, 2002

(54) SYRINGE

(76) Inventor: Frank C Hill, 9 Medical Pk #510, Columbia, SC (US) 29203

(*) Notice: Subject to any disclaimer, the term of this patent is extended or adjusted under 35 U.S.C. 154(b) by 0 days.

(21) Appl. No.: 09/428,367

(22) Filed: Oct. 28, 1999

(51) Int. Cl.[7] ............................................. A61M 5/315
(52) U.S. Cl. ..................................................... 604/218
(58) Field of Search ................................. 604/218, 187, 604/181, 188, 239, 240

(56) References Cited

U.S. PATENT DOCUMENTS

| | | |
|---|---|---|
| 3,118,447 A | 1/1964 | Hunt et al. |
| 3,388,941 A | 6/1968 | Marcus |
| 4,217,896 A | 8/1980 | Behnke |
| 4,324,241 A | 4/1982 | Reese |
| 4,351,334 A | 9/1982 | Inglefield, Jr. |
| 4,687,472 A | 8/1987 | Gross |
| 4,801,263 A * | 1/1989 | Clark ........................... 433/90 |

* cited by examiner

Primary Examiner—Brian L. Casler
Assistant Examiner—Ann Y Lam
(74) Attorney, Agent, or Firm—Sara A. Centioni; Nexsen Pruet Jacobs & Pollard LLC

(57) ABSTRACT

An improved syringe that allows one-handed operation, without requiring the user to reposition her hands during any portion of the injection process. The syringe comprises a housing having a plunger disposed therein that expels medication through a needle when the plunger is pressed toward the opposing end wall. Instead of having the needle in the same axis as the plunger, the needle port is carried by the wall of the syringe housing at an acute angle with respect to the longitudinal axis of the housing. With this configuration, the housing can be gripped between a finger and thumb, with the one of the fingers on the handle and the other finger on the end wall of the housing. A pair of rings are positioned at opposing ends of the housing receive the user's fingers so that relative movement of the finger and thumb creates both suction as well as pressure for injection of medication from the housing's chamber.

20 Claims, 1 Drawing Sheet

SYRINGE

FIELD OF THE INVENTION

The present invention relates to syringes that are used for injecting medication.

BACKGROUND OF THE INVENTION

Injecting medication is a somewhat cumbersome process, involving repositioning of the hands and excessive movement after the syringe needle has been inserted into the tissue. Conventional syringes are constructed with the plunger immediately behind and aligned with the axis of the needle. Because of this arrangement and the need to insert the syringe needle and then to check its position in the tissue before injecting medication, the user must manipulate the syringe twice during the process.

The person administering the injection is required to perform several steps. First, the user will hold the syringe like a dart in order to have a firm grip while inserting the needle. Upon inserting the needle into the injection site, the user will reposition his hands so as to be able to pull the plunger out slightly, creating a small amount of suction, in order to verify that the tip of the needle is not in a blood vessel. Next, the user must again reposition his hands to push the plunger and thereby inject medication into the tissue. This injection process is not only cumbersome and inefficient, but may also cause needless discomfort to the patient.

Therefore, there is a need for an improved syringe that would reduce excess movement of the hands during an injection.

SUMMARY OF THE INVENTION

According to its major aspects and broadly stated, the present invention is an improved syringe that does not require the user to reposition his hands during any portion of the injection. The syringe comprises a housing having a plunger slidably disposed therein for expelling medication through a needle when the plunger is pressed. Instead of having the needle aligned with the same axis of the plunger, however, the needle port is located on the side of the housing at an angle with respect to the longitudinal axis of the plunger. This frees the end wall of the housing for the index finger of the user, to be used in opposition to the thumb pressing the handle of the plunger. With this configuration, the housing can be gripped between a finger and thumb, with one of the fingers on the handle and the other finger on the end wall of the housing. Rings on the plunger handle and end wall of the housing enable better control especially when pulling the plunger slightly to create suction in the housing.

A major feature of the present invention is the angle between the plunger and needle port. With this arrangement, the ends of the syringe can be held by the thumb and index finger, with the needle extending off to the side at an angle. This feature allows the present syringe to be held in the same position with the same hand during insertion of the needle and throughout the injection process. Upon insertion of the needle, the user simply separates his fingers to create suction in order to determine if the tip of the needle is in a blood vessel. Next, the user simply squeezes his fingers together to inject the medication into the patient. During both operations, the present syringe is held in the same dart-like fashion as it is for inserting the needle into the tissue.

A major advantage of the present invention is that the present syringe is held in the same way throughout the injection process with no need to reposition the hands of the one administering the injection. This allows the procedure to be performed more quickly and without the discomfort that results from lateral movement of the needle of the prior art syringe during repositioning of the hands.

Another feature of the present invention is the use of rings on the syringe. With the rings, the user can move the plunger in either direction easily, expelling the medication and creating suction, without removing or repositioning his hands on the syringe.

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

Figure 1:
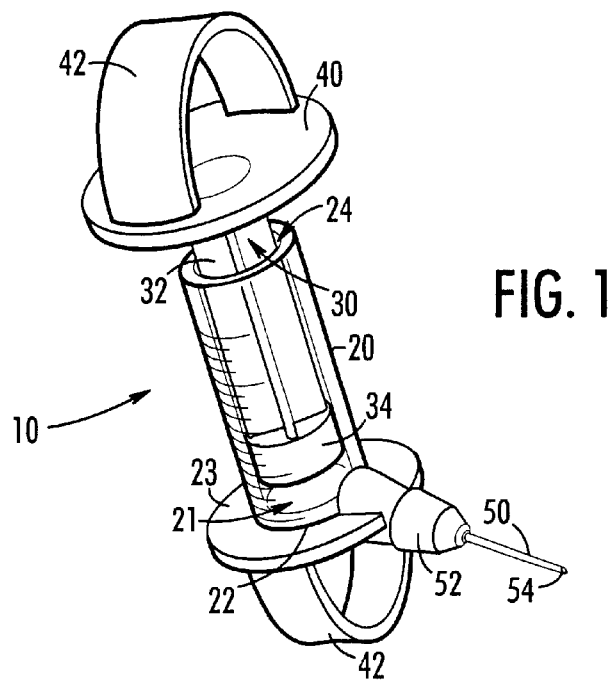
FIG. 1 is a perspective view of a syringe, according to a preferred embodiment of the present invention.

The present invention is an improved syringe that allows one-handed operation. Referring to FIG. 1, syringe 10 comprises a housing 20 having a plunger 30 disposed therein. Plunger 30 enables the expulsion of a liquid, such as a liquid medication, through a needle 50 upon moving plunger 30 from a first position near an open end 24 of housing 20 to an opposing end wall 22 of housing 20. End wall 22 of housing 20 can preferably be held against the pressure on plunger 30 with a finger or thumb 100 in a ring 42; plunger 30 can similarly be held by a finger or thumb at a ring 42 so that squeezing or separating the two fingers 100 changes the volume inside housing 20. Rings 42 make separating fingers 100, and with them plunger 30 and housing 20, easier.

Figure 2:
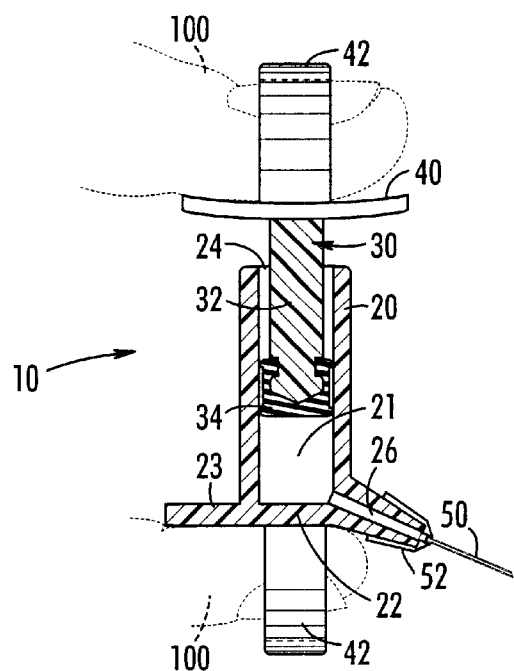
FIG. 2 is a side cross-sectional view of a syringe, according to a preferred embodiment of the present invention.

Referring to FIG. 2, housing 20 preferably has a cylindrical wall made of any translucent suitable material such as glass, plastic, or the like. Housing 20 has a chamber 21 therein, defined by the interior of the wall of housing 20 and plunger 30, which chamber 21 is capable of holding a quantity of liquid. Housing 20 has an open end 24 that receives plunger 30 and an opposing end wall 22. Plunger 30 is free to slide from open end 24 to end wall 22. Housing 20 has a port 26, preferably defined by an extension of the wall of housing 20 and that is disposed at an angle with respect to the longitudinal axis of plunger 30. The particular angle is not critical so long as the user can place a finger 100 on end wall 22 without interfering with needle 50. Needle 50 preferably extends radially outward at an acute angle with respect to the long axis of housing 20. By acute angle, it is meant that the angle is less than 90° when measured with respect to the long axis of housing 20 as it extends through and past end wall 22.

To aid in accurate and secure placement of a finger on end wall 22, end wall 22 preferably has a flange 23 that serves as a platform for the finger 100 and ring 42 to hold end wall 22 while plunger 30 and end wall 22 move with respect to each other. Port 26 is a passage through the wall of housing 20 for the liquid to pass from housing 20 and through the bore formed in hollow needle 50. Needle hub 52 allows the frictional fit of needle 50 to syringe 10 so that lumen 54 (FIG. 1) of needle 50 is in fluid communication with chamber 21 via the bore of needle 50.

A plunger 30 is slidably disposed within housing 20. Plunger 30 has a shaft 32 with a handle 40 at one end and a seal 34 at the opposing end. Seal 34 is made of any suitable material that provides fluid-tight, frictional engagement with the walls of housing 20 when sliding between open end 24 of housing 20 and end wall 22, preferably a natural or synthetic rubber or resilient plastic.

Rings 42 are positioned on handle 40 and end wall 22 that are dimensioned to receive the user's fingers 100. If the user squeezes his fingers 100 together when fingers 100 are in rings 42, thereby applying a force on handle 40 which moves seal 34 toward end wall 22 while end wall 22 is held fixed, the volume of chamber 21 is reduced and thereby medication is expelled from housing 20. If the user separates his fingers 100 while they are inserted in rings 42, force will be placed upon handle 40 to move plunger 30 toward open end 24 of housing 20, thereby enlarging the volume of chamber 21 and creating a suction force at lumen 54.

In use, the user grips the housing 20 using a finger 100 in each ring 42. With this type of a grip on the housing 20 and needle 50 pointed away from the hand of the user, the user can easily insert the needle 50 into the tissue at the injection site. By separating the user's fingers 100, and creating a slight suction force at lumen 54, the user can determine whether the needle 50 has been inserted into a blood vessel (a small volume of blood would appear in chamber 21 if it were). Next, the user can squeeze his fingers 100 together, thereby injecting the medication from chamber 21 through port 26 and the bore of needle 50 into the injection site.

It will be apparent to those skilled in the art that many changes and substitutions can be made to the preferred embodiment herein described without departing from the spirit and scope of the present invention.

LIST OF COMPONENTS
(For convenience Of The Examiner)

| 10 | syringe |
|---|---|
| 20 | housing |
| 21 | chamber |
| 22 | end wall |
| 23 | flange |
| 24 | open end |
| 26 | port |
| 30 | plunger |
| 32 | shaft |
| 34 | seal |
| 40 | handle |
| 42 | ring |
| 50 | needle |
| 52 | needle hub |
| 54 | lumen |

What is claimed is:

1. A syringe, comprising:
   a housing having a chamber that is dimensioned for holding a quantity of liquid, said housing having a first end and an opposing second end, said second end of said housing having a port formed therein, said port being at an angle with respect to the longitudinal axis of said housing;
   a plunger slidably disposed within said housing;
   a first ring carried by said plunger;
   a second ring carried by said second end of said housing;
   a needle having a bore extending therethrough and in fluid communication with said chamber through said port, said needle being between said first ring and said second ring; and
   means carried by said second end of said housing for applying an opposing pressure on said plunger so that said plunger can be moved toward said second end of said housing, said plunger expelling the liquid in said chamber when said plunger is moved toward said second end.

2. The syringe as recited in claim 1, wherein said port extends radially from the longitudinal axis of said housing.

3. The syringe as recited in claim 1, wherein said angle is an acute angle.

4. The syringe as recited in claim 1, wherein said first ring is dimensioned to receive a finger.

5. The syringe as recited in claim 1, wherein said second ring is dimensioned to receive a finger.

6. A syringe comprising;
   a housing having a chamber that is dimensioned to hold a quantity of liquid, said housing having a wall, a first end and an opposing second end, said second end of said housing having a port formed therein, said port being at an angle with respect to the longitudinal axis of said housing;
   a handle carried by said housing;
   a first ring carried by said handle;
   a second ring carried by said second end of said housing;
   a hollow needle carried by said wall of said housing and having a bore extending therethrough in fluid communication with said chamber via said port, said needle being between said first ring and said second ring; and
   plunger means responsive to squeezing said handle and said second end of said housing together in order to expel the liquid from said chamber, said housing and said plunger means defining the volume of said chamber.

7. The syringe as recited in claim 6, wherein said plunger means is responsive to movement of said handle relative to said second end of said housing for creating pressure in said chamber.

8. The syringe as recited in claim 6, wherein said second ring is dimensioned to receive a finger.

9. The syringe as recited in claim 8, further comprising a second ring carried by said second end of said housing, said ring dimensioned to receive a finger.

10. The syringe as recited in claim 9, wherein said port extends radially from the longitudinal axis of said housing.

11. A syringe comprising:
    a housing having a chamber that is capable of holding a quantity of liquid, said housing having a first end and an opposing second end, said second end of said housing having a port that is at an angle with respect to the longitudinal axis of said housing;
    a handle carried by said housing, said handle movable with respect to said second end of said housing;
    a first ring carried by said handle;
    a second ring carried by said second end of said housing;
    a hollow needle having a bore therethrough, said needle carried by said housing so that said port and said chamber are in fluid communication with each other; said needle being between said first ring and said second ring; and
    plunger means responsive to the movement of said handle and expelling the liquid from said chamber when said plunger is moved toward said second end of said housing.

12. The syringe as recited in claim 11, wherein said plunger means is responsive to squeezing said handle and said second end of said housing towards each other.

13. The syringe as recited in claim 11, wherein said plunger means is responsive to pulling said handle and said second end of said housing away from each other for creating a negative pressure in said chamber.

14. The syringe as recited in claim 11, wherein said first ring is dimensioned to receive a finger.

15. The syringe as recited in claim 11, wherein said second ring is dimensioned to receive a finger.

16. The syringe as recited in claim 11, wherein said port extends radially from the longitudinal axis of said housing.

17. The syringe as recited in claim 11, wherein said angle is an acute angle with respect to the longitudinal axis of said housing.

18. A syringe, comprising:
- a housing having a chamber that is dimensioned for holding a quantity of liquid, said housing having a first end in spaced relation to a second end;
- a plunger slidably disposed within said housing;
- a first ring carried by said plunger;
- a second ring carried by said second end of said housing;
- a needle having a bore extending therethrough and in fluid communication with said chamber, said needle being between said first ring and said second ring;
- means carried by said second end of said housing for applying pressure on said plunger so that said plunger can be moved toward said second end of said housing, said plunger expelling the liquid in said chamber when said plunger is moved toward said second end.

19. A syringe, comprising;
- a housing having a chamber that is dimensioned to hold a quantity of liquid, said housing having a first end and a second end;
- a handle carried by said housing;
- a first ring carried by said handle;
- a second ring carried by said second end of said housing;
- a needle carried by said housing and having a bore extending therethrough in fluid communication with said chamber, said needle being between said first end and said second end; and
- plunger means responsive to squeezing said handle and said second end of said housing together in order to expel the liquid from said chamber.

20. A syringe, comprising:
- a housing having a chamber that is capable of holding a quantity of liquid, said housing having a first end and a second end in spaced relation to said first end, said second end of said housing having a port formed therein;
- a plunger slidably disposed within said housing;
- a first ring carried by said plunger;
- a second ring carried by said second end of said housing;
- a needle having a bore extending therethrough and in fluid communication with said chamber through said port, said needle being between said first ring and said second ring; and
- plunger means responsive to movement of said handle and expelling the liquid from said chamber when said plunger is moved toward said second end of said housing.

\* \* \* \* \*